US006448788B1

(12) United States Patent
Meaney et al.

(10) Patent No.: US 6,448,788 B1
(45) Date of Patent: Sep. 10, 2002

(54) FIXED ARRAY MICROWAVE IMAGING APPARATUS AND METHOD

(75) Inventors: Paul M. Meaney; Keith D. Paulsen, both of Hanover; Margaret W. Fanning, Etna, all of NH (US)

(73) Assignee: Microwave Imaging System Technologies, Inc., Hanover, NH (US)

( * ) Notice: Subject to any disclaimer, the term of this patent is extended or adjusted under 35 U.S.C. 154(b) by 0 days.

(21) Appl. No.: 09/580,309

(22) Filed: May 26, 2000

Related U.S. Application Data

(60) Provisional application No. 60/136,010, filed on May 26, 1999.

(51) Int. Cl.[7] ................ G01R 27/32; H01Q 21/00; A61B 5/05; G06F 17/10
(52) U.S. Cl. ................ 324/637; 324/639; 343/853; 600/407; 703/2
(58) Field of Search ................ 324/637, 639, 324/632, 645, 638; 703/2; 600/407; 343/852, 853

(56) References Cited

U.S. PATENT DOCUMENTS

| 5,621,331 | A | * | 4/1997 | Smith et al. | 324/645 |
| 5,649,064 | A | * | 7/1997 | Jorgensen | 706/17 |
| 5,841,288 | A | * | 11/1998 | Meaney et al. | 324/639 |
| 6,295,392 | B1 | * | 9/2001 | Gregory et al. | 382/321 |

OTHER PUBLICATIONS

Microwave image reconstruction utilizing log–magnitude and unwrapped phase to improve high–contrast object recovery Meaney, P.M.; Paulsen, K.D.; Pogue, B.W.; Miga, M.I. IEEE Transactions on Medical Imaging, vol. 20 Issue: Feb. 2, 2001.*
Nonactive antenna compensation for fixed–array microwave imaging. I. Model development Paulsen, K.D.; Meaney, P.M. Medical Imaging, IEEE Transactions on , vol.: 18 Issue: Jun. 6, 1999 pp.: 496–507.*
Nonactive antenna compensation for fixed–array microwave imaging. II. Imaging results Meaney, P.M.; Paulsen, K.D.; Chang, J.T.; Fanning, M.W.; Hartov, A. Medical Imaging, IEEE Transactions on , vol.: 18 Issue: Jun. 6, 1999 pp. 508–518.*

P. M. Meaney, K. D. Paulsen, J. T. Chang, M. Fanning, "Towards a Clinical Implemenation of a Non–Invasive Microwave Imaging . . . ," *SPIE*, vol. 3249.0277–786X/98.

P. M. Meaney, K. D. Paulsen, J. T. Chang, "Forward Solution Match Issues Affecting Iterative Inverse Scattering Approaches," (source unknown).

K. D. Paulsen, P. M. Meaney, "Nonactive Compensation For Fixed Array Microwave Imaging: Part I—Model Development," *IEEE Trans. on Med. Imag.*, 1998.

P. M. Meaney, K. D. Paulsen, John T. Chang, M. W. Fanning, A. Hartov, "Nonactive Compensation For Fixed Array Microwave Imaging: Part II—Imaging Results," *IEEE Trans. on Med. Imag.*, 1998.

\* cited by examiner

*Primary Examiner*—N. Le
*Assistant Examiner*—Anjan K. Deb
(74) *Attorney, Agent, or Firm*—Curtis A. Vock, Esq.; Thomas Swenson, Esq.; Lathrop & Gage, L.C.

(57) ABSTRACT

An improved method and apparatus for microwave imaging of an inhomogeneous target, in particular of biological tissue, compensates for the interactions between active antennae and nonactive antennae. Measured electric field data are processed in magnitude and phase form so that unwrapped phase information may be used directly in the image reconstruction. Initial finite element measurements and calculations are used to determine the perimeter dimensions of the target being examined, resulting in more accurate image reconstructions. An improved regularization technique is a hybrid of a Marquardt regularization scheme with a spatial filtering technique and a Tikhonov regularization scheme. An improved switching matrix enables simultaneous sampling of electric field data from a plurality of receiving antennae.

35 Claims, 6 Drawing Sheets

FIXED ARRAY MICROWAVE IMAGING APPARATUS AND METHOD

This application claims the benefit of U.S. Provisional Application No. 60/136,010 May 26, 1999.

GOVERNMENT SUPPORT

This invention was made in part with government support under contract number RO1-CA55034 awarded by the National Institute of Health. The government of the United States has certain rights in the invention.

BACKGROUND OF THE INVENTION

1. Field of the Invention

The invention relates to electromagnetic imaging of inhomogeneous, lossy targets having arbitrary shape, and in particular, it relates to microwave imaging to reconstruct electrical properties of biological tissue.

2. Statement of the Problem

Active microwave imaging for medical diagnosis is known in the art. U.S. Pat. No. 5,841,288, issued Nov. 24, 1998 to Meaney et al., discloses an apparatus and methods for determining electrical properties of an inhomogeneous target. The electrical property distribution on an arbitrary coarse mesh distribution of the target is first estimated; then corresponding electric field values on a fine mesh distribution of the target are computed. The fine mesh has finer discretization than the coarse mesh and is overlapping with the coarse mesh. Electric field values are then measured at preselected measurement sites within a homogeneous region external to the target. A Jacobian matrix is calculated, which represents a sensitivity calculation relative to a change in the electric field values at selected measurement sites due to a perturbation in the electrical property distribution on the coarse mesh. A difference vector is formed between the computed electric field and the measured electric field values, and an update vector is added to the electrical property distribution as a function of the difference vector and the Jacobian matrix. The electric field values are then re-computed based on the updated electrical property distribution, which is compared with the measured electric field values to produce a least squared error. If this error is not sufficiently small, the steps above, beginning with computing a Jacobian matrix, are repeated until the error is sufficiently small.

The dual mesh scheme reduces the number of points where electrical properties $\in_r$ and $\sigma$ are calculated within a region of interest. The fine mesh is uniformly dense and is used for calculating the electric field values over the region; the coarse mesh is less dense, can be uniform or non-uniform, and is used for representing the $k^2$ distribution within the region. The term "$k^2$" is the complex wavenumber, squared, and includes both electrical properties $\in_r$ and $\sigma$, (i.e., $k^2 = \omega \mu \in_o \in_r + j\omega \mu \sigma$, where $\in_o$ is the dielectric constant in a vacuum, $\in_r$ is the relative dielectric constant, $\sigma$ is the conductivity, and $\mu$ is the magnetic permeability of free space). The number of nodes on the coarse mesh is less than or equal to the number of individual pieces of measurement data. The dual mesh scheme thus utilizes a practical amount of measurement data and the calculation of the $k^2$ distribution is performed without compromising the accuracy of the forward solution.

Such known methods and systems provide a calibration routine to convert 3-D measured data to a 2-D format. Such a routine is utilized because microwave antennae radiate into 3-D space; yet, the reconstruction algorithms typically utilize only 2-D radiation characteristics. This is important because of the nature of antennae: in 3-D, the free space loss factor (FSLF) varies proportionally to $1/R^2$ from the phase center of a transmitting antenna; while in 2-D, the FSLF varies proportionally to $1/R$ (R equals the distance from the phase center to the receiver). Thus, this approach substitutes the data's dependency on $1/R^2$ with a dependency on $1/R$. Specifically, a calibration routine calculates the phase center of each antenna and then modifies the amplitude relative to the $1/R^2$ and $1/R$ dependencies. The phase center is calculated by measuring the electric fields at a number of points within the homogeneous medium. A least squares procedure then determines where the phase center must have been to give such a field distribution.

In calculating the electrical property distribution of a target, the following equation is solved for the electric field vector, $\vec{E}$, at each iteration:

$$[A]\{\vec{E}\} = \{\bar{b}\},$$

where $[A]$ is the forward solution matrix, and $\{\bar{b}\}$ is a vector representing the boundary condition. The derivative is then taken with respect to the electrical properties for every coarse mesh node $i$ and every radiating transmitter antenna:

$$\left[\frac{\partial A}{\partial k_i^2}\right]\{\vec{E}\} = -[A]\left\{\frac{\partial E}{\partial k_i^2}\right\}.$$

Note that $\{\bar{b}\}$ is not a function of the electrical property distribution so its derivative with respect to $k_i^2$ is zero. This equation is used to solve for $$\left\{\frac{\partial E}{\partial k_i^2}\right\},$$

since $[A]$, $\vec{E}$ are already known. A matrix $$\left[\frac{\partial A}{\partial k_i^2}\right]$$

is thus formed, in which its coefficients are the derivatives of the individual terms of the matrix $[A]$ used in the forward solution of the electric fields. These coefficients are computed with respect to the electrical properties, $k_i^2$, at a single node on the coarse mesh. This new mesh, in combination with the original matrix $[A]$ used in the computation of the electric fields and the most current calculated values of the electric field, $\vec{E}$, is used to compute the variations of the electric fields due to perturbation of the electrical properties, e.g., $$\left\{\frac{\partial E}{\partial k_i^2}\right\},$$

at a single coarse mesh node, for a single radiator. The terms $$\left\{\frac{\partial E}{\partial k_i^2}\right\}$$

make up the Jacobian matrix. Thus, to build the whole Jacobian matrix, the process is repeated for all of the radiators and all of the nodes. This time-consuming process can be efficiently done in parallel.

Typically, the inhomogeneous target object being analyzed is surrounded by a homogeneous medium contained in an illumination chamber. Transmitter and receiver antennae are disposed in the homogeneous region surrounding the object. Typically, the homogeneous medium is a saline bath or other liquid solution. Measuring the electric field includes irradiating the target with microwave energy having a single operating frequency from a plurality of transmitting antennae that surround the target, and receiving microwave energy at a second plurality of receiving antennae for each of the transmitting antennae. Typically, the antennae are arranged substantially within the same plane about the target. Computing the electric field includes computing, through simulation, the electric field at finite element nodes on the fine mesh. Determining electrical property distributions includes estimating the electrical property values based upon a homogeneous distribution with values identical to the homogeneous medium surrounding the target. Computing an electric field includes computing a two-dimensional field distribution utilizing hybrid element techniques. In such a technique, the electric field values are determined by finite element discretization of the target region and a small portion of the homogeneous region immediately surrounding the target region, in combination with the boundary element method to represent the outer surrounding homogeneous region. The step of discretizing the target with a finite element mesh (that is, the fine mesh) may include minimizing the number of nodes on the fine mesh.

An illumination chamber comprises material that is lossy within the operating frequency range, which is about 300 MHz to 1100 MHz in the prior art. The illumination chamber may have a thick solid wall, for example in a cylindrical or square shape, surrounding the target, and in which the antennae are disposed. Typically, however, the illumination chamber contains a liquid homogeneous medium, in which the target is disposed. Transmitting and receiving antennae are suspended within the liquid homogeneous medium to surround the target. Electrical property distributions are determined through a coarse mesh discretization of the illumination region, which includes the target region and homogeneous region. The fine mesh representing the target region is arbitrarily shaped.

Microwave imaging systems provide several advantages. First, they provide a method of determining the 2-D electrical property distributions of electrically nonuniform targets, which is relevant to the measure of human tissue due to the large contrast range of electrical properties. By way of example, bone and fat typically have a relative dielectric constant of about 5.0–6.0 at 500 MHz, while the dielectric constant of an aqueous based tissue (for example liver, kidneys and muscle) is more on the order of 50 to 70. The large contrast can be exploited in numerous applications, such as: 1) breast cancer detection, where the typical ex vivo breast tissue has a relative dielectric constant, $\in_r$, of about 15, while a malignant breast tumor has a relative dielectric constant, $\in_r$, in the range of 65–75; 2) the measurement of air and water content within tissue, because air has a dielectric constant, $\in_r$, of 1.0, and the dielectric constant, $\in_r$, of water is close to 75.

The spatial locations of the antennae surrounding a target must be precisely known to achieve accurate measurements of the electric field values and accurate computations with the finite element model. Preferably, the antennae are located all in a horizontal plane at a known vertical position. It is also important for the antennae to be able to reach and take measurements in positions suited to detect and measure electrical characteristics throughout the target object.

One of the complexities associated with realizing a viable medical microwave imaging system is the undesirable coupling of the imaging transceiver antennae with the surrounding environment (other than the biological target of interest). This problem is particularly acute in electronically scanned microwave arrays that typically consist of multiple transmit/receive antennae in close proximity. With the antenna array configurations typically utilized in the clinical interface in the art, the presence of non-active antennae perturbs the electromagnetic field patterns significantly, which can degrade the recovered images.

Also, electric field phase changes due to high contrast scattering by objects, like the breast, within the illumination region can often exceed $\pi$ radians. As a result, information may be lost with regards to the object under interrogation since conventional imaging schemes use the data and a format that restricts the range of possible phase values to the range of $-\pi$ to $+\pi$ radians.

Furthermore, exact dimensions of the target object, the target perimeter, at a given imaging plane are typically unknown. Data acquisition typically uses non-contacting antennae; thus, the target perimeter cannot be deduced accurately a priori, and this may compromise the accuracy of the calculations. In a typical method and apparatus of the prior art, a fine mesh is used for computing the electric field values at each iteration, and a course mesh is used for reconstructing the electrical properties within the target region. Because of typically high contrast in electrical properties between the surrounding saline solution and the target tissue, such a technique may be able to recover only an outline of the target and to achieve only minimal resolution of heterogenities within the target tissue. Essentially, the computational task of recovering the steep gradient at the target/saline bath interface overwhelms the more subtle task of recovering the map of a electrical property inhomogenities within the target tissue.

SOLUTION

In methods and apparati for determining electrical properties of an inhomogeneous target, which include measuring electric field values external to a boundary that defines the target using an antenna array, in which an active transmitting antenna transmits a microwave signal, an active receiving antenna receives the microwave signal, and in which undesired coupling may occur between a nonactive antenna and the active antennas, improvements in accordance with the invention comprise methods and systems for compensating the coupling between the nonactive antenna and the active antennas.

Features of the invention include: modeling each nonactive antenna as an electromagnetic sink; presenting a matched termination to all nonactive antennae via a coaxial connection to either a coaxial matched load, a matched switch, or a well-matched amplifier; computing electric field values at the nonactive antennae; modeling the nonactive antennae as finite diameter cylinders having a surface, with a radiation type boundary condition imposed on the surface; empirically determining an effective radius and an effective impedance of the nonactive antennae. Empirically determining the effective radius and the effective impedance usually comprises measuring electric field values at a plurality of frequencies, preferably in a range of from 300 MHz to 3 GHz. Empirically determining the effective radius and the effective impedance typically includes measuring an electric field value when the nonactive antennae are present and when the nonactive antennae are not present.

In methods and apparati for determining electrical properties of an inhomogeneous target, including steps of measuring electric field values external to a boundary that defines the target using an antenna array having a plurality of antennae, in which an active transmitting antenna transmits a microwave signal, and an active receiving antenna receives the microwave signal, the invention provides an improvement including computing an amplitude and a phase value of the electric field values. Features of the invention include: unwrapping the phase value of the electric field values. Unwrapping the electric field values may include unwrapping of scattered computed 2D forward data. Unwrapping of scattered computed 2D forward data typically includes: calculating electric field values at a plurality of computation points between the antennae; choosing a reference computation point close to the active transmitting antenna; and comparing phase values at the computation point and a neighboring computation point to determine an unwrapped phase value at the neighboring computation point. Unwrapping the electric field values also typically include unwrapping scattered field data, which entails: determining a first unwrapped phase value at the active receiving antenna at a first, low frequency; measuring a second, wrapped phase value at the receiving antenna at a second, higher frequency; and then comparing the second, wrapped phase value with the first, unwrapped phase value to determine a second, unwrapped phase value. This procedure is repeated for all frequencies until the phases at all frequencies for each receiver have been unwrapped.

In determining electric field properties of an inhomogeneous target, including steps of measuring electric field values external to a boundary that defines the target, estimating electric property distributions in a coarse mesh discretization of the target, and computing an electric field in a fine mesh discretization of the target and at points external to the fine mesh discretization, the invention provides improvements including: performing a first reconstruction, thereby determining a perimeter of the target; and calculating a new fine mesh and a new coarse mesh, the new meshes conforming to the perimeter. In one aspect of the invention, the target is surrounded by a homogeneous medium, and the perimeter corresponds to an interface between the target and the homogeneous medium. The homogeneous medium typically is a saline bath. A target typically comprises biological tissue. Methods and apparati in accordance with the invention are particularly well-suited for determining electrical properties of a human female breast.

In methods and apparati for determining electric field properties of an inhomogeneous target, including steps of measuring electric field values external to a boundary that defines the target, estimating electric property distributions in a coarse mesh discretization of the target, and computing an electric field in a fine mesh discretization of the target and at points external to the fine mesh discretization, the invention provides an improvement including: using a Marquardt regularization scheme combined with a Tikhonov regularization scheme. Typically, the Marquardt scheme provides an initial guess of the electrical property distributions, and the Tikhonov scheme thereafter recovers a refined image of the electrical property distributions.

In systems and apparati for determining electrical properties of an inhomogeneous target, comprising an illumination chamber containing a homogeneous medium having substantially homogeneous electrical properties and in which the inhomogeneous target may be disposed, and an antenna array having a plurality of antennae disposed within the homogeneous medium for transmitting and alternately receiving microwave energy, the invention provides an improvement characterized in that the system comprises an A/D board capable of simultaneously sampling the downconverted signals received by a plurality of the antennae. Preferably, the system operates over a frequency band in a range of from 300 MHz to 3 GHz. The homogeneous region preferably comprises a saline solution. A system in accordance with the invention may comprise a microwave switching network for selecting one channel for signal transmitting and either one or multiple channels simultaneously for signal receiving. A system in accordance with the invention may comprise presenting a matched termination to all non-active antennae via a coaxial connection to either a matched switch (as the last element of the switching matrix) or a single pole-double throw (SPDT) switch connected to a well-matched amplifier. A system may be further characterized in that the antenna array may comprise a plurality of inverted monopole antennae and in that the antenna array is movable to multiple vertical positions. Preferably, a system comprises an electronically controllable linear translation stage for vertically moving the antenna array. The antenna array may be mounted to a solid array plate. Preferably, the system comprises protective bellows for protecting electrical wires connected to the antennae. A system typically includes a sheet of solid material disposed above the homogeneous medium and the illumination tank, and having a hole for accommodating the inhomogeneous target. In particular, such a rigid sheet is capable of supporting a human patient and has a hole for accommodating a human body part.

Numerous other features, objects and advantages of the invention will become apparent from the following description when read in conjunction with the accompanying drawings.

DETAILED DESCRIPTION OF THE PREFERRED EMBODIMENT

1. Overview

Figure 1:
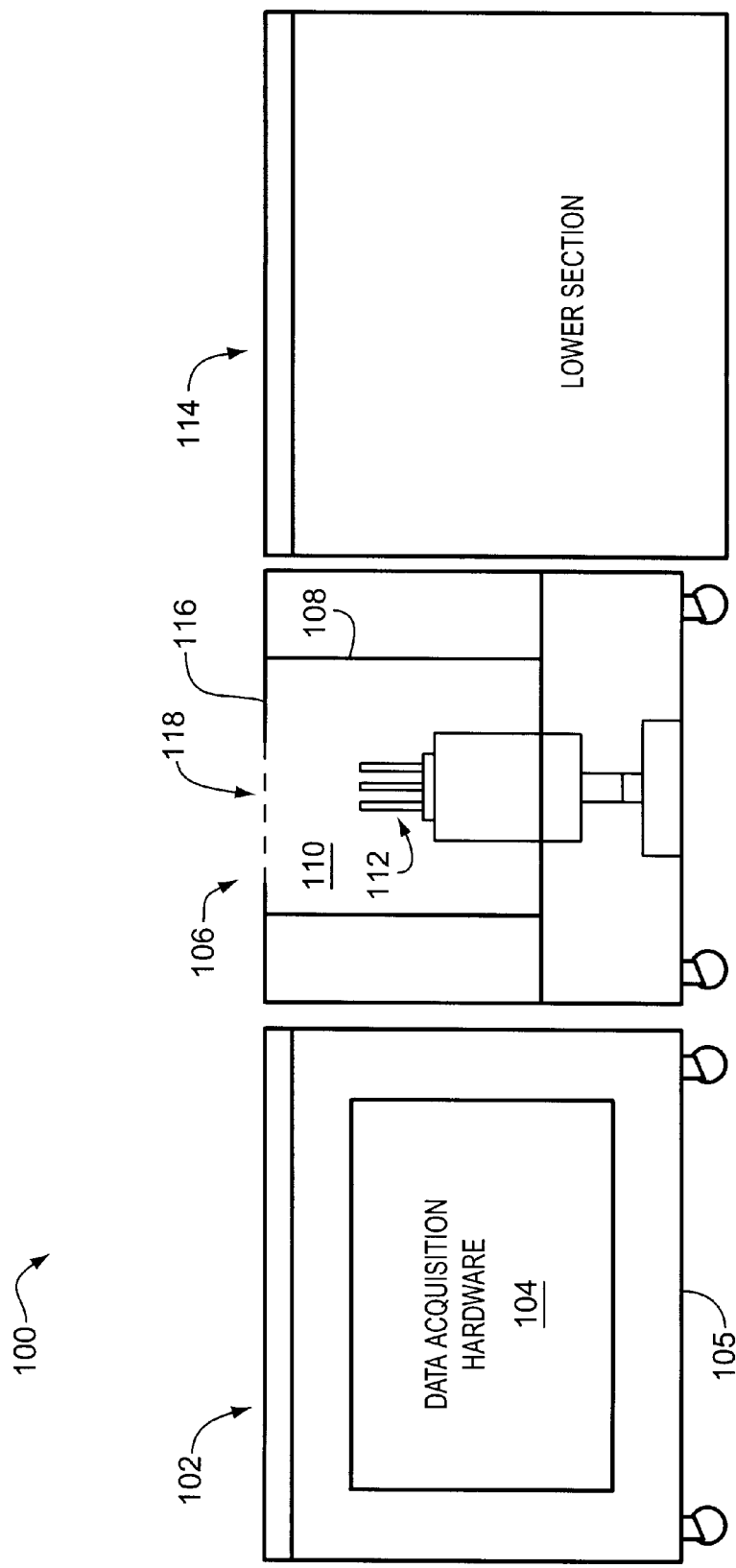
FIG. 1 depicts a patient bed comprising data acquisition hardware and a clinical interface section.

The present invention provides novel improvements to methods and systems used in the art, for example, to the apparatus and method described in U.S. Pat. No. 5,841,288, issued Nov. 24, 1998 to Meaney et al., which is hereby incorporated by reference as if fully contained herein. A method and a system in accordance with the present invention are discussed herein with reference to microwave imaging of a human female breast for diagnostic purposes. It is understood, however, that the invention is useful for electromagnetic imaging of many types of inhomogeneous targets.

Inversion of the monopole antenna array is a key aspect of this invention. In cases of breast cancer, a large number of tumors originate close to the chest wall. Thus, in a system in accordance with the invention, the antennae are oriented so that the active section of each antenna is as close to the plane of the patient chest wall as possible to facilitate imaging close to the chest wall. The present configuration of the inverted monopole antenna may have a cable assembly originating from underneath the center of the saline tank. A protective bellows surrounding the cables and fixtures protects them from the saline bath or other homogeneous medium, and also serves as a seal to prevent water from leaking out of the tank. The antennae are mounted to a solid array plate that can be raised and lowered through the manipulation of a hydraulic jack positioned beneath the plate. In an alternative embodiment, the hydraulic jack can be replaced with an electronically controllable positioning motor. In an alternative embodiment, two electronically controllable linear translation stages are mounted on opposite sides of the illumination tank. The array plate to which the monopole antennae are mounted expand out horizontally in two directions to attach to the translation stages. These may move up and down in a coordinated fashion. This allows vertical positioning of the array to be controlled by the central computer to speed up data acquisition and minimize operator involvement and potential error. A preferred embodiment of an apparatus in accordance with the invention comprises a 32 channel network, with all ports capable of being electronically selected for either transmit or receive mode.

Data acquisition hardware may be disposed on a portable cart, which can be positioned directly up against the illumination tank apparatus. It is important that the electronics on the cart are physically close to the antennae to minimize possible interface problems, such as cable standing waves.

Preferably, the apparatus includes an HP4432B I & Q synthesized source, that combines the functions of the microwave source, function generator, division of the CW signal into two components, and the I & Q modulation of the signal. The system operates over a wide frequency band, preferably about 300 MHz to 3 GHz, with the higher frequencies having shorter signal wavelengths to achieve better image resolution. Additionally, instead of only being able to sample one receive signal at a time, the preferred switching network design, in conjunction with a parallel sampling A/D board, allows simultaneous sampling of signals from all of the receive antennae associated with a given transmit antenna.

A system in accordance with the present invention provides a liquid based clinical interface, preferably with a circular array of upwardly oriented monopole antennae. The entire array is translatable to multiple vertical positions for acquiring data at predefined coronal planes of the breast.

A method and a system in accordance with the present invention include a compensation scheme that improves the match between the actual illumination region and the numerical model, and subsequently improves image quality. An improved numerical formulation compensates for the coupling of the nonactive antennae associated with array operation. A method in accordance with the invention further includes a technique to utilize unwrapped phase information in the reconstruction algorithm, which improves image quality.

While in operation, a system in accordance with the invention transmits a known microwave signal from a transmitting antenna, and then records that signal in a modified form as it is received by a single receiving antenna. The transmitting antenna and the receiving antenna are referred to as a transmitter/receiver antenna pair. Other antennae in the antennae array are referred to as "nonactive" antennae.

A novel antenna array model incorporates antenna-to-antenna interactions. Two-dimensional implementation of this antenna array model improves the data-to-model match between the measurements and the computations, which in turn leads to improved image reconstructions from experimental data. The nonactive antennae are essentially modeled as electromagnetic "sinks". In this context, a "sink" is referred to as something where the fields may interact or "be coupled to it", but may not exit or be re-radiated. According to the model, all power coupled to nonactive antennae is not re-radiated back into the homogeneous medium in which the antennae are located. The physical antenna is a monopole. For purposes of a numerical model, each antenna is represented as a finite diameter cylinder with a radiation-type boundary condition imposed on its surface. Therefore, modeling it as a sink entails constructing a circular boundary of some radius and imposing radiation boundary conditions with an appropriate impedance. The effective radius and impedance at a plurality of frequencies are determined empirically. This mathematical construct is convenient in terms of accurately representing the switching network configuration of a data acquisition system.

In conjunction with the mathematical representation, the actual switching matrix is constructed such that its last stage is a matched switch or a single pole-double throw (SPDT) switch with a well-matched amplifier attached to it. Therefore, even when an antenna channel is in its nonactive state, any signal coupled to any antenna and propagated up a coaxial cable is terminated at the switch or amplifier without re-radiation by the antenna, which is precisely the behavior represented in the model. Thus, the physics of the switching matrix configuration matches that of the numerical model quite well. The effective radii and impedances at each frequency are determined empirically. Hence, the novel method includes both mathematical modeling of non-active antenna compensation and an empirical calibration procedure, conducted using homogeneous conditions. As a result, it improves the data-model match through both more advanced modeling and incorporation of antenna-specific measurement data.

Further, a method and system in accordance with the invention create a first image of the target object with a uniform coarse mesh to determine the target perimeter. Then, a new set of meshes is produced with the perimeter of the new meshes conforming to the targevsaline bath interface.

2. Description of Preferred Embodiment

Figure 2:
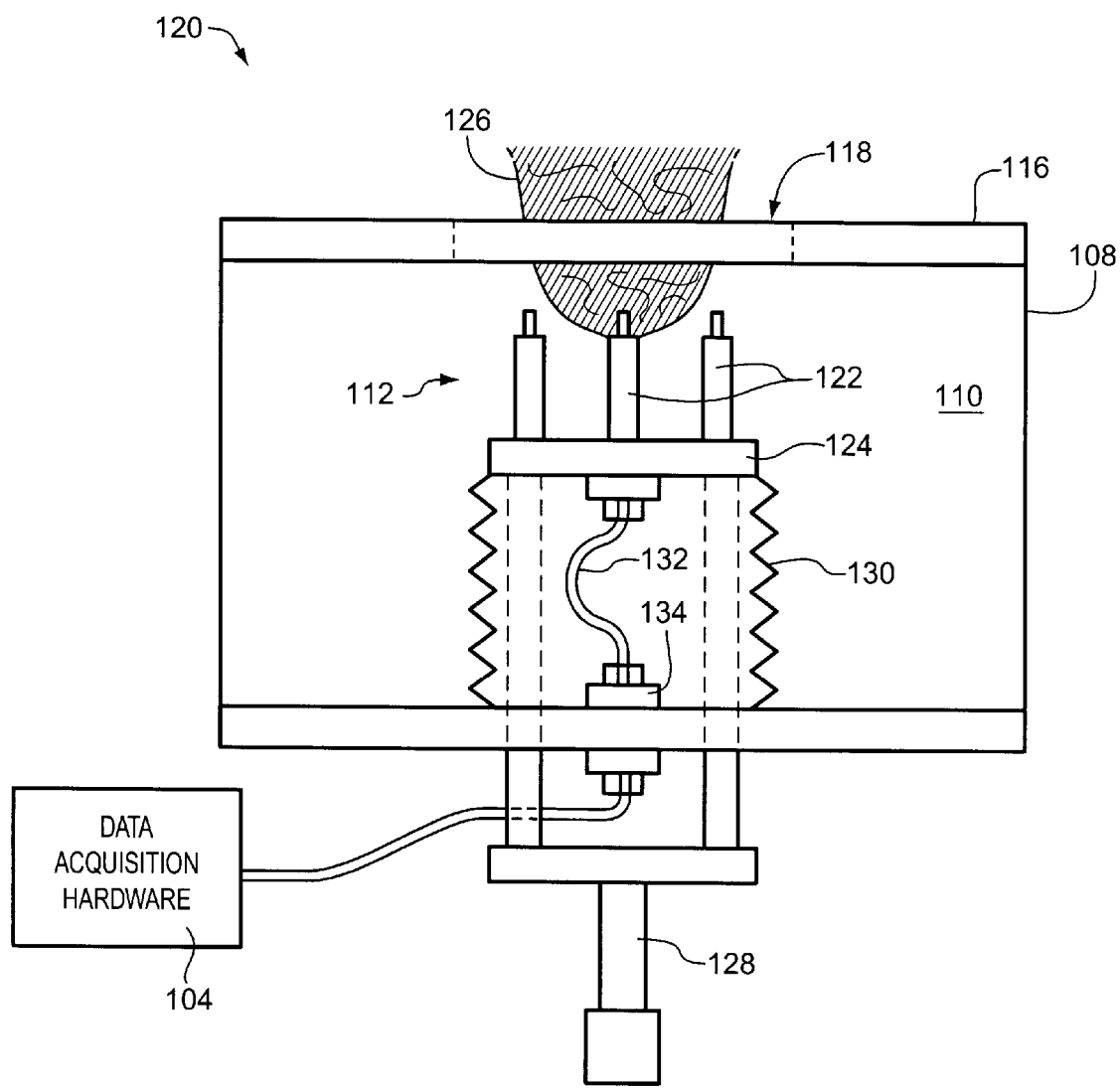
FIG. 2 depicts monopole antennae mounted to a vertically movable solid array plate.
Figure 3:
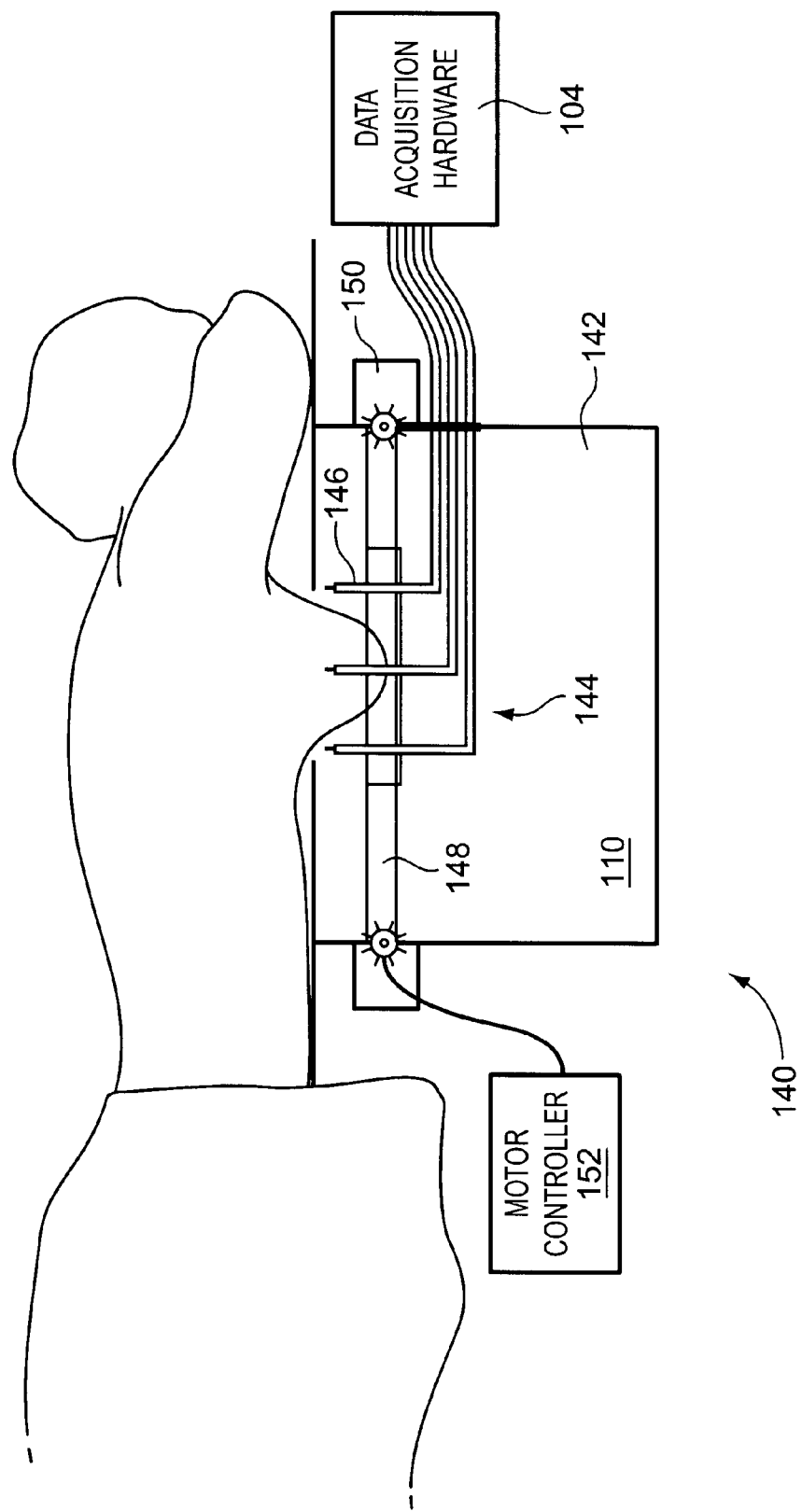
FIG. 3 depicts an alternative embodiment in which monopole antennae are mounted in an atenna array that is attached to linear translation stages.

In FIG. 1, a cross-sectional view of a patient bed 100 in accordance with the invention is depicted. Patient bed 100 comprises three sections: a head area 102, under which all of the data acquisition hardware 104 resides; the clinical interface section 106, containing illumination chamber 108, liquid homogeneous region 110, and antenna array 112; and the lower section 114, where the lower part of the patient rests. The top surface 116 of illumination chamber 108 contains an aperture 118, through which the human breast being imaged protrudes so that the breast is pendant in a liquid homogeneous region 110. Liquid homogeneous region 110 typically comprises a saline bath. Data acquisition system 104 is preferably mounted on a portable cart 105, which can be positioned directly up against the illumination tank section 106. It is important that electronics on cart 105 be physically close to the antennae to minimize possible interface problems, such as cable standing waves. The sketch of FIG. 2 depicts in more detail a portion 120 of section 106. Monopole antennae 122 mounted to solid array plate 124 extend upwards vertically to surround a portion of a human female breast 126, which extends through aperture 118 into homogeneous saline bath region 110. In a preferred embodiment, antenna array 112 contains up to 32 (thirty-two) monopole antennae 122. Monopole antennae 122 and antennae array 112 are vertically movable by means of hydraulic jack 128, which is connected to solid array plate 124. Flexible bellows 130 surrounds cables 132, which are connected to monopole antennae 122 and extend through sealing 134 out of illumination chamber 108 to data acquisition system 104. In FIG. 3 is depicted an alternative embodiment 140 of an illumination tank section. Illumination tank section 140 comprises illumination tank 142 in which antenna array 144 is disposed. Monopole antennae 146 are mounted in antennae array plate 148, which is attached to linear translation stages 150. Linear translation stages 150 are controlled and moved vertically by vertical motorized controller 152.

Figure 4:
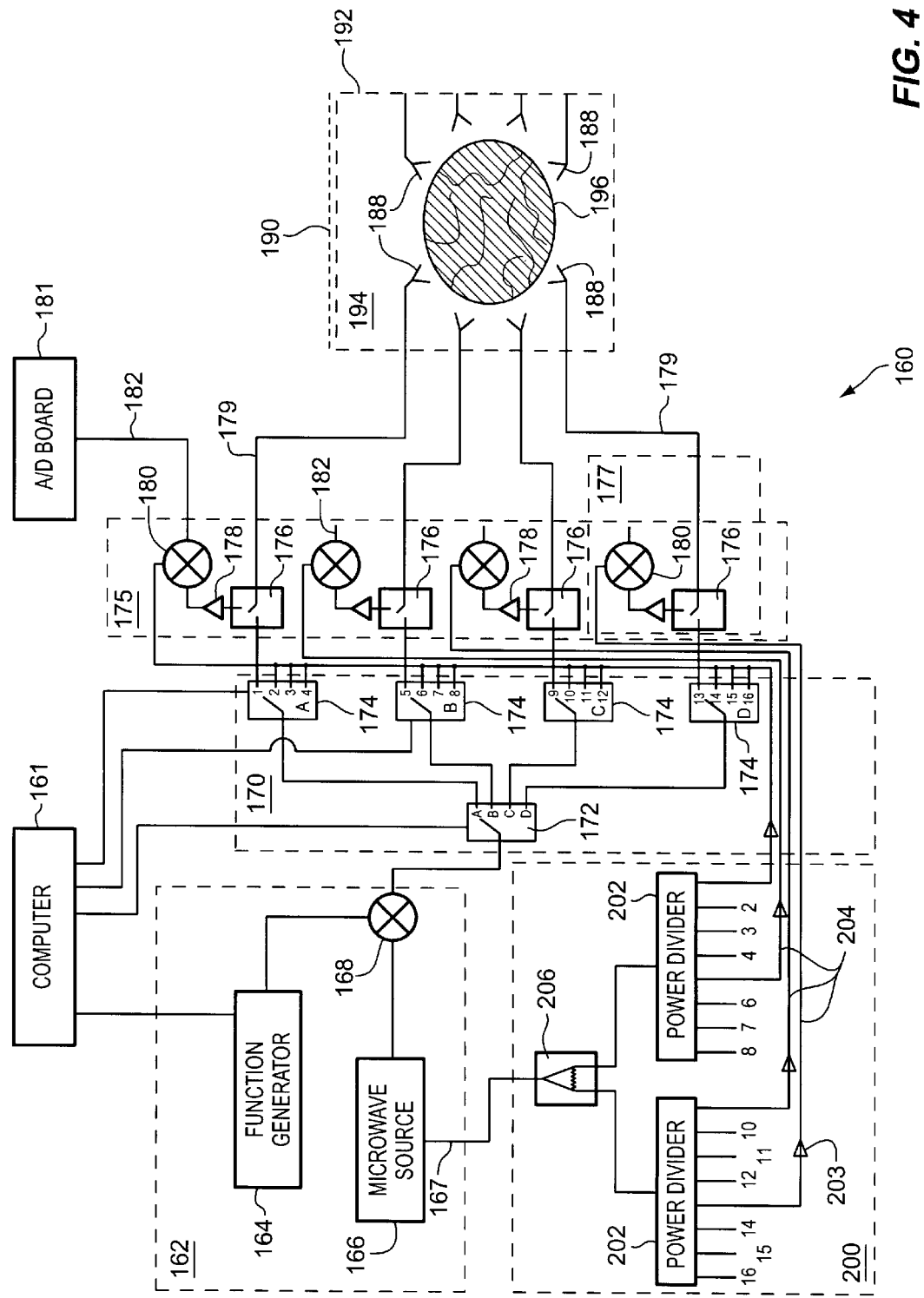
FIG. 4 contains a diagram of a data acquisition system.

The sketch of FIG. 4 contains a diagram 160 of data acquisition system 104. In a preferred embodiment, data acquisition system 104 comprises a model HP 4432B I & Q synthesized source 162. Signal generator 162 combines the functions of a microwave source 166, function generator 164, division of the CW signal in the two components 166, and the I & Q modulation 168 of the transmitted signal. The system 104 operates over the frequency band of 300 MHz to 3 GHz for reduced signal wavelength at higher frequencies and better image resolution. An important feature of improved data acquisition system 104 is a switching network design (in conjunction with a parallel sampling A/D board) that allows simultaneous sampling of signals from all receive antennae associated with a given transmitter.

The corporate-fed switch matrix 170 utilizes cascaded single pole-4 throw (SP4T) switches 172 and 174 to propagate the modulated signal from the HP 4432B I & Q synthesized source 162 to a single transceiver module 177 for eventual transmission by a monopole antenna 188. Each SP4T switch 172 and 174 is electronically controllable through TTL inputs from the computer 161 to select one of the four outputs for a given input signal. Diagram 160 of the data acquisition system 104 shows only a 16-channel system but can easily be expanded to 32 channels. The array 175 of transceiver modules comprises individual transceiver modules 177. Each transceiver module 177 comprises a single pole-double throw (SPDT) switch 176 which alternates between allowing a transmit signal to propagate from the switch matrix 170 to a monopole antenna 188 for transmission, to receiving a signal from the monopole antenna 188 and directing it to a Low Noise Amplifier 178, followed by a microwave mixer 180 to produce a low frequency IF output signal 182, which can be sampled by the A/D board 181 and recorded digitally by the computer 161. Each mixer 180 in the array 175 of transceiver modules 177 requires an unmodulated reference signal 204 to combine with the received signal to produce a downconverted IF signal 182. The unmodulated reference LO signal 167 is sent from the microwave source 166 to the LO power divider network 200. It is split into two equal amplitude signals by a two-way power divider 206 to feed two eight-way power dividers 202 to produce 16 output LO signals 204. In practice, each eight-way power divider 202 comprises seven two-way power dividers 206. This LO power divider network 200 can also be readily expanded from 16 channels to 32 channels. Because of the reduction in LO signal strength from repeated signal divisions by the power dividers 206 and 202, the LO signals 204 require amplification by microwave amplifiers 203 prior to input to the microwave mixers 180. The LO signals are also in the microwave frequency range. The output of a mixer 180 is a low-frequency downconverted signal 182, generally in the range of 1–20 kHz. The downconverted signal 182 can then be sampled by the A/D board. Since the A/D board can digitize multiple signals in parallel, the downconverted signals 182 that were originally received by a plurality of antennae can be sampled simultaneously.

The RF signal 179 propagating between each transceiver module 177 and its associated monopole antenna 188 (or 122 in FIG. 2) also passes through the cables 132 and the plate sealing 134. The antennae are submerged in the saline bath 194 contained in the illumination chamber 192 of the illumination tank section 190. FIG. 4 shows the antennae 188 surrounding the target region 196.

The signals received by the monopole antennae 188 are propagated to the SPDT 176 of the transceiver modules 177 and directed to the low noise amplifier 178. The impedance perceived by the monopole antennae 188 must be well matched. This impedance is defined by the cascade of the SPDT 176 and the low noise amplifier 178. Since the SPDT 176 is well matched and simply redirects the signal to the low noise amplifier 178, the individual impedance match of the low noise amplifier 178 dominates the effective impedance match of the cascade of the SPDT 176 and the low noise amplifier 178. The impedance match of the low noise amplifier 178 is defined as a voltage standing wave ratio (VSWR) of better than 1.22:1. It should be noted that the impedance characteristics of the microwave mixer 180 have negligible effect on the impedance seen by the monopole antennae 188.

A saline solution used in accordance with the invention typically comprises a solution of sodium chloride in water. Such a saline bath typically has a 0.9% (by weight) concentration. A water-based surrounding medium presents a considerable contrast with normal breast tissue in terms of $\in_r$, which could inhibit imaging with the tissue. However, recent results suggest this contrast is considerably less for in vivo breast tissue. Thus, water may still be a suitable coupling medium for breast examinations. Water has the advantage that it is cheap, readily available, and can be cleaned out of the illumination tank quickly. Alternative liquids with low dielectric constants include heavy sugar mixtures and various alcohols.

An important feature of a preferred embodiment in accordance with the invention is that data about each subject can be quickly collected over a broad frequency range. At high frequencies, the physical receive antenna separation is electrically large enough to render unwrapping the phase data with respect to adjacent receiver data impossible. However, by collecting the data over a broad frequency range, the data can be easily unwrapped at the lowest frequency, and the data for each transmit receive antenna pair for successive frequencies can be easily unwrapped by comparison with corresponding data from the previous frequency.

In accordance with the invention, a hybrid element approach is used for image reconstruction. The hybrid element approach deploys the finite element method inside the biological target of interest where the electromagnetic property distribution is expressed in a piecewise linear basis function expansion whose coefficients are to be determined. Also, a boundary element method discretizes the uniform surrounding space, which comprises an attenuating homogeneous medium, in which the electromagnetic radiating antennae are disposed. The boundary element method exactly accounts for unbounded wave propagation of any scattered fields and efficiently approximates the physical situation where finite walls confine the external attenuating medium, but reflections are essentially non-existent because of the severe signal decay.

A transverse magnetic ("TM") mode wave propagation model is assumed. The starting point is the scalar Helmholtz equation, representing the electric field component perpendicular to the imaging plane $$\nabla^2 E_z + k^2 E_z = -f \quad (1)$$

where $E_z$ is the electric field component of interest, $k^2$ is the square of the electromagnetic wavenumber whose real ($k_R^2 = \omega^2\mu\in$) and imaginary ($k_I^2 = \omega\mu\sigma$) components are the quantities to be reconstructed and $f = \delta(x_s, y_s)$ is the electromagnetic radiator having line source amplitude A positioned at location $(x_s, y_s)$. Standard Galerkin finite element treatment of (1) inside the biological target leads to the weighted residual statement $$\langle \nabla E_z \cdot \nabla \phi_i \rangle - \langle k^2 E_z \phi_i \rangle = \oint \hat{n} \cdot \nabla E_z \phi_i ds \quad (2)$$

where $\phi_i$ is the ith member of a set of N piecewise continuous Lagrange polynomials, < > indicates integration over the biological target, and $\oint$ represents its enclosing surface, with $\hat{n}$ being the outward pointing direction normal to that surface. Note that $f=0$ in the finite element portion of the problem space because the antennae are located in the boundary element zone. $E_z$ is the basis-function expanded in the same set of piecewise continuous polynomials which produces the matrix system $$\begin{bmatrix} A_{II} & A_{Ib} \\ A_{bI} & A_{bb} \end{bmatrix} \begin{Bmatrix} E_I \\ E_b \end{Bmatrix} = \begin{bmatrix} 00 \\ 0B_{bb} \end{bmatrix} \begin{Bmatrix} 0 \\ F_b \end{Bmatrix} \quad (3)$$

where subscript I refers to basis/weighting function polynomials associated with nodes in the finite element region that are not on the boundary (i.e. strictly interior) while subscript b refers to discretization points on the biological region boundary. Here $E_I$ and $E_b$ are the electric field values at the interior and boundary nodes, respectively, whereas $F_b$ is the flux (i.e. $F = \nabla E_z \cdot \hat{n}$) at the boundary nodes. $A_{1I}$, $A_{1b}$, $A_{bI}$, $A_{bb}$ and $B_{bb}$ are submatrices involving integrations of the known $\phi$ functions according to equation (2) when the weighting and basis functions are centered either both on interior nodes (i.e. $A_{1I}$), one is centered on the interior nodes and the other on boundary nodes (i.e. $A_{1b}$, $A_{bI}$), or both are centered on boundary nodes ($A_{bb}$, $B_{bb}$).

The boundary element discretization is based on the integral equation statement for calculating the electric field at any point in the homogeneous boundary element region of the problem domain $$\alpha_i E_{zi} = \oint (G_i (\nabla E_z \cdot \hat{n}) - (\nabla G_i \cdot \hat{n}) E_z) ds + \langle fG_i \rangle \quad (4)$$

to where $G_i$ is the unbounded space Green's function (singular at node i) for the 2-D Helmholtz equation (in this case, the Hankel function) having an argument that is the product of the exterior region wavenumber times the distance from node i to the integration path, $\alpha$ is the fractional portion of the integral path around node i ($\alpha=1$ for a node interior to the boundary element region and $\alpha=\frac{1}{2}$ for a node located on a smooth portion of the boundary element integration path). Expanding $E_z$ in the same type of piecewise continuous Lagrange polynomial and moving the Green's function singularity to each boundary node in turn generates the matrix system $$[D_{bb}]\{E_b\} = [C_{bb}]\{F_b\} + \{Z_b\} \quad (5)$$

where the b subscript refers to the same boundary nodes denoted in equation (3), $Z_b$ is the source-term column vector whose entries are $z_i = \langle fG_i \rangle$ for each boundary node. $D_{bb}$ and $C_{bb}$ are matrices involving the integration of known quantities around the boundary which separates the boundary element and finite element spaces and have entries $d_{ij} = \alpha_i + \int \nabla G_i \cdot \hat{n} \phi_j ds$ and $c_{ij} = \oint G_i \phi_j ds$, respectively.

Hybrid solution for the complete imaging system space when the electromagnetic properties are known (or estimated) involves inverting $C_{bb}$ in (5) in order to solve for $F_b$ and substituting this result into (3) yielding $$\begin{bmatrix} A_{II} & A_{Ib} \\ A_{bI} & A_{bb} - B_{bb}C_{bb}^{-1}D_{bb} \end{bmatrix} \begin{Bmatrix} E_I \\ E_b \end{Bmatrix} = \begin{bmatrix} 0 & 0 \\ 0 & -B_{bb}C_{bb}^{-1} \end{bmatrix} \begin{Bmatrix} 0 \\ Z_b \end{Bmatrix} \quad (6)$$

Once (6) is solved for the electric field everywhere in the finite element region, the boundary values, $E_b$, can be used in (5) to compute $F_b$ which together are incorporated into (4) to deduce $E_z$ anywhere in the boundary element region (i.e. node position i in equation (4) can be located at any interior point within the boundary element domain once $E_b$ and $F_b$ are known). In discrete form, a column vector of electric field values at each imaging system measurement position can be computed as $$\{E_x\} = [D_{xb}]\{E_b\} + [C_{xb}]\{F_b\} + \{Z_x\} \quad (7)$$

where $E_x$ are the electric fields calculated at the set of measurement sites $x_1, x_2 \ldots x_m$ outside the target region, and Dxb, Cxband $Z_x$ are similar to their counterparts in equation (5) except that the distance used in the Green's function argument extends from each measurement site to the boundary element integration path.

The electric field values computed at each measurement site according to Equation (7) represent an approach in which imaging data were collected with a single transmit/receive antenna pair. The approach incorporates a model of the antenna transmitter through $Z_x$ in equation (7) and equivalently $Z_b$ in equation (5), but does not include the influence of neighboring nonactive antennae on the measured values as would occur during data collection from an imaging array of transceiver elements. The values calculated by (7), which are intended to match the measurement data from the imaging system, are completely independent of one another; hence, they do not represent a satisfactory model of fixed antenna array measurements in practice where a certain amount of neighboring antenna interactions typically occur.

Figure 5:
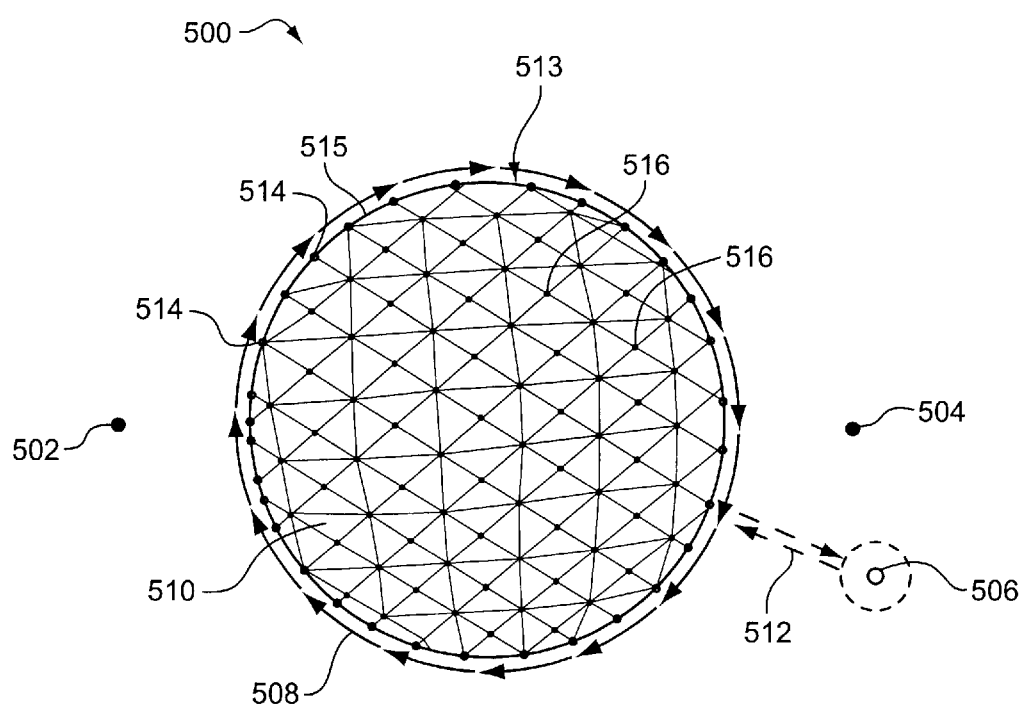
FIG. 5 is a schematic representation of a transmitter antenna and a receiver antenna in the presence of a single nonactive array element.

A method and apparatus in accordance with the invention provide a marked improvement over the basic approach represented by Equations (1)–(7). To account for neighboring antenna interactions during data collection from a fixed array, a model in accordance with the invention compensates for the presence of the nonactive antennae of the measurement array during each illumination of the biological target of interest. Specifically, the nonactive antennae (i.e., all other antennae but the source-receiver pair) are modeled as a set of line elements on which an impedance boundary condition is applied. A schematic of the computational domain 500 is shown in FIG. 5. FIG. 5 shows a transmitter, or source, antenna 502 and receiver antenna 504 in the presence of a single nonactive array element 506. The novel integration path 508 (compared to that used to develop Equations (5) and (7)), includes a path around target 510, as well as an excursion 512 around the nonactive antenna elements 506. This additional integration around the nonactive antenna elements 506 is the key to incorporating the novel antenna compensation model. The target 510 is modeled as a finite element mesh 513, which has boundary nodes 514 on the target boundary 515, and internal nodes 516 internal to the target boundary 515. For simplicity, the case of a single nonactive antenna is discussed, but the approach readily generalizes to multiple nonactive antennae as would exist during fixed array data acquisition.

Figure 6:
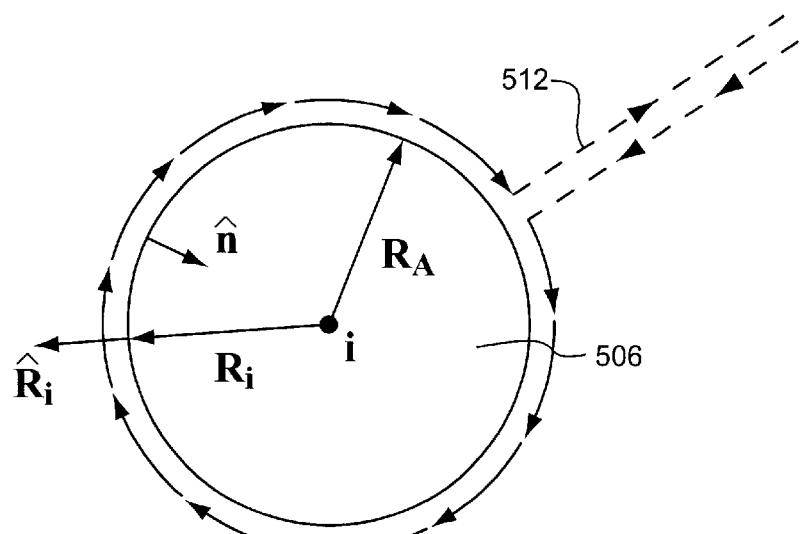
FIG. 6 depicts the computational integration path around a nonactive antenna when the Green's function singularity is positioned at the nonactive antenna center.
Figure 7:
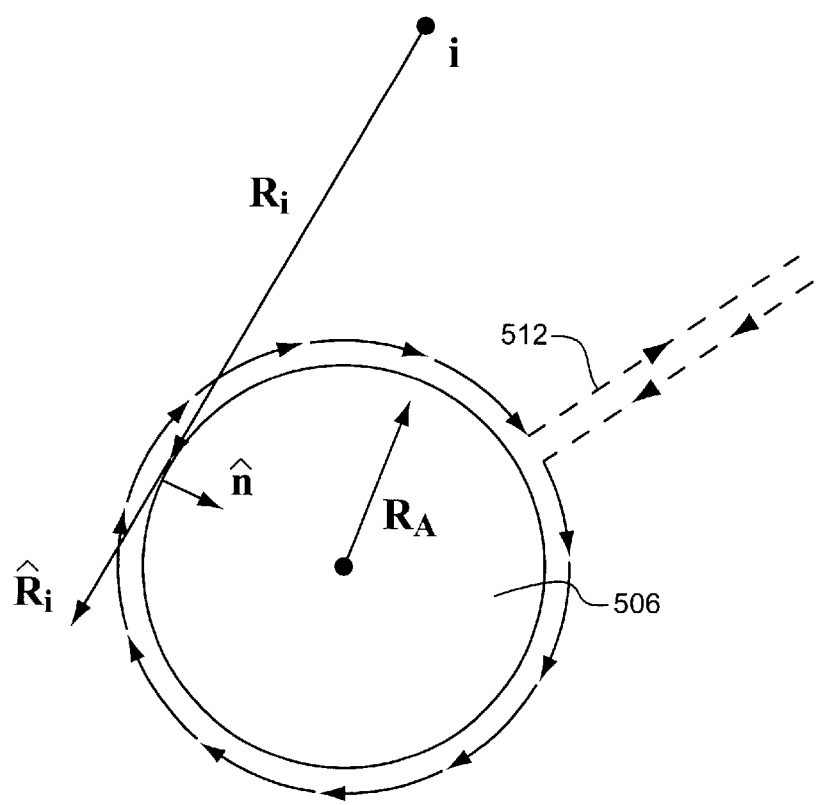
FIG. 7 depicts the computational integration path around a nonactive antenna when the Green's function singularity is positioned elsewhere along the integration path.

The nonactive antenna contour alters the integrations and concomitant matrix elements in Equation (5) in two ways: (a) when the Green's function singularity is positioned at the nonactive antenna center 506; and (b) when the Green's function singularity is positioned elsewhere along the integration path. Schematics of these two situations are depicted in FIG. 6 and FIG. 7, respectively, and the details of their incorporation into equation (5) are considered in turn. The Green's function singularity is positioned at node "i" for both cases depicted in FIG. 6 and FIG. 7. For case (a) in FIG. 6, the integrations around the target boundary are straightforward and proceed as usual with the distance quantity in the Green's function argument being measured from the center of the nonactive antenna to the integration path point along the target boundary. When the integration path proceeds around the nonactive antenna itself (see FIG. 6), the boundary integral along this position of the contour becomes $$\oint_{antenna} \left( \frac{\partial E}{\partial n} G_i - \frac{\partial G_i}{\partial n} E \right) ds \approx \quad (8)$$

$$\frac{\partial E_i}{\partial n} G_i \int_0^{2\pi} R_A d\Theta - \frac{\partial G_i}{\partial n} E_i \int_0^{2\pi} R_A d\Theta$$

under the assumption that the antenna radius, $R_A$, is electrically small enough that E and $\nabla E \cdot \hat{n}$ are essentially constant along the integration path (note that G and $\nabla G \cdot \hat{n}$ are constant at a fixed distance from the singularity at the antenna center). The integral contribution in Equation (8) can be further simplified to $$\oint_{antenna} \left( \frac{\partial E}{\partial n} G_i - \frac{\partial G_i}{\partial n} E \right) ds \approx 2\pi R_A \left[ \frac{\partial E_i}{\partial n} G(kR_A) + E_i \frac{\partial G_i}{\partial R}(kR_A) \right] \quad (9)$$

where and $\partial_n G_i = \partial_R G_i(\hat{R}_i \cdot \hat{n})) = -\partial_R G_i$ (here, $\partial_x$ is a short-hand notation for the partial derivative with respect to x). Since there is only a single integral equation statement centered at each nonactive antenna, but two additional unknowns, $E_i$ and $\partial_n E_i$, arise, a second relationship is invoked:

$$E_i = -j\gamma \frac{\partial E_i}{\partial n} \quad (10)$$

as an impedance boundary condition at the antenna where $j=\sqrt{-1}$ and $\gamma$ is the effective impedance factor, to eliminate one variable:

$$\oint_{antenna} \left( \frac{\partial E}{\partial n} G_i - \frac{\partial G_i}{\partial n} E \right) ds \approx \frac{\partial E_i}{\partial n} 2\pi R_A \left[ G_i(kR_A) - j\gamma \frac{\partial G_i}{\partial n}(kR_A) \right] \quad (11)$$

Hence, the integral around the nonactive antenna when the singularity in G is located at its center (FIG. 6) produces contributions to the diagonal of the C matrix of equation (5).

In case (b) of FIG. 7, when the singularity in G is positioned on the imaging region boundary (or another nonactive antenna center), but the integration path occurs around the nonactive antenna (see FIG. 7), it is assumed that E and $\partial_n E$ are essentially constant over this segment of the integration path, leading to the contribution $$\oint_{antenna} \left( \frac{\partial E}{\partial n} G_i - \frac{\partial G_i}{\partial n} E \right) ds \approx \frac{\partial E_A}{\partial n} \left[ \int_0^{2\pi} G_i(kR_i(\Theta)) R_A d\Theta \right] - \quad (12)$$

$$E_A \left[ \int_0^{2\pi} \frac{\partial G_i}{\partial R}(kR_i(\Theta)) \hat{R}_i(\Theta) \cdot \hat{n}(\Theta) R_A d\Theta \right] \approx$$

$$\frac{\partial E_A}{\partial n} R_A \left[ \int_0^{2\pi} G_i(kR_i(\Theta)) d\Theta + j\gamma \int_0^{2\pi} \frac{\partial G_i}{\partial R}(kR_i(\Theta)) \hat{R}_i(\Theta) \cdot \hat{n}(\Theta) d\Theta \right]$$

where $E_A$ and $\partial_n E_A$ are the field and flux on the antenna surface, respectively.

The right hand side of equation (12) is easily integrated with Gaussian quadrature or can be further approximated as $$\frac{\partial E_A}{\partial n} R_A \left[ 2\pi R_A G_i(kR_i) + j\gamma \frac{\partial G_i}{\partial R}(kR_i) \int_0^{2\pi} \hat{R}_i(\Theta) \cdot \hat{n}(\Theta) d\Theta \right] \approx \quad (13)$$

$$\frac{\partial E_A}{\partial n} 2\pi R_A G_i(kR_i)$$

when the distance from the singularity to the nonactive antenna is large compared to $R_A$ (i.e., $R_i \gg R_A$) since $$\int_0^{2\pi} \hat{R}_i(\Theta) \cdot \hat{n}(\Theta) d\Theta$$

vanishes in this case. As in Equation (11), the integration in Equation (12) produces a contribution to the C matrix of (5) in the column associated with antenna A. In effect, $\partial_n E$ is computed at the nonactive antenna site, and through equation (10), E is deduced at that location as needed. Building these relationships into the boundary element equations leads to an expanded matrix system related to (5) that can be written as $$\begin{bmatrix} D_{bb} & 0 \\ D_{Ab} & 0 \end{bmatrix} \begin{Bmatrix} E_b \\ 0 \end{Bmatrix} = \begin{bmatrix} C_{bb} & C_{bA} \\ C_{Ab} & C_{AA} \end{bmatrix} \begin{Bmatrix} F_b \\ F_A \end{Bmatrix} + \begin{Bmatrix} Z_b \\ Z_A \end{Bmatrix} \quad (14)$$

where the $C_{bA}$ terms have the form of equation (12) and the $C_{AA}$ terms appear similarly to that of equation (11). Once (14) is assembled, complete solution proceeds by inverting C in order to solve for $F_b$ $$\{F_b\} = [Cl_{bb} D_{bb} + Cl_{bA} D_{Ab}]\{E_b\} - [Cl_{bb}]\{Z_b\} - [Cl_{bA}]\{Z_A\} \quad (15)$$

and substituting this expression into (3) to produce $$\begin{bmatrix} A_{II} & A_{Ib} \\ A_{bI} & A_{bb} - B_{bb} G_{bb} \end{bmatrix} \begin{Bmatrix} E_I \\ E_b \end{Bmatrix} = \begin{Bmatrix} 0 \\ -B_{bb}([Cl_{bb}]\{Z_b\} + [Cl_{bA}]\{Z_A\}) \end{Bmatrix} \quad (16)$$

where $G_{bb} = Cl_{bb} D_{bb} + Cl_{bA} D_{Ab}$ and $Cl = C^{-1}$. This formulation provides two parameters, $R_A$, and $\gamma$, the effective nonactive antenna radius and impedance, which can be used to fit calculated results to measured data when the imaging region is assumed to be known.

The perturbations of the electric field measurements due to the presence of the nonactive antennae are used to determine the effective radius and impedance of each antenna. In general, these perturbations in both magnitude and phase can be quite small. Hence, it is imperative to implement procedure for collecting this data that minimizes all other types of measurement error. An approach used in the best contemplated method is summarized in the following steps:

1) Position the full complement of antennae in the illumination region, while connecting only a single transmit/receive antennae pair to the switching matrix of the data acquisition system. Terminate all of the nonactive antennae with a coaxial matched load.

2) Record the field measurements for the case of no objects present within the illumination region over a broad range of frequencies.

3) Record the field measurements for the cases of various known phantoms at certain locations within the illumination region over the same range of frequencies.

4) Remove the nonactive monopole antennae from the illumination region, being careful not to perturb to transmit/receive antennae pair or any of the associated coaxial cables.

5) Repeat steps to 3 immediately for the case without the nonactive antennae present.

6) Repeat steps 1 through 5 for all transmit/receiver antenna pair.

While the monopole antennae are designed so that they can be removed from the array relatively easily, in general this procedure is quite tedious due to the large number of antennae elements; hence it is practical to collect a set of data for all of the transmitter/receiver pairs associated with only a single transmitter. For the case of homogeneous illumination region, extra data sets that might be collected utilizing other transmitters are essentially replicas of this single data set due to the array symmetry, and do not provide new information. For the data collected with various objects present, the positions of the objects are chosen to produce a range of representative nonactive antenna effects.

While this measurement configuration is not identical to that utilized in the data collection scheme at the time of imaging (during acquisition, all antennae are connected via coaxial cables to the last element of the switching matrix or a single pole-double throw (SPDT) switch and well-matched amplifier of the transceiver module), it is reasonably representative of the impedance matches seen by the nonactive antennae at the time of data acquisition. This is because the last element of the switching matrix or the SPDT with amplifier are deliberately chosen to have characteristic return losses of better than 20 dB in either the "on" or the "off" state.

The values of the effective antenna radius and associated impedance must be computed empirically using an iterative linear regression technique. To accomplish this task, differences between the measured amplitudes (in decibels) and phases (in degrees) are first determined from the data sets collected in Step 3 of the measurement procedure described of both. Corresponding sets of data are also produced using the numerical model for the associated cases with and without the presence of the nonactive antennae. Three pairs of initial guesses for the effective antenna radius and impedance are chosen to initialize the procedure. A linear regression is then employed to deduce new values of these parameters, which produce the closest fit in a least squares sense between the measured and computed field differences, respectively. Subsequently, three new pairs of radius and impedance values are chosen in the proximity of the most recently computed quantities. The procedure is repeated until it converges to an optimal pair of radius and impedance parameters.

Beginning with the hybrid element (HE) method which involves the coupling of a finite element (FE) representation for the inhomogeneous target region with a boundary element (BE) representation for the homogeneous surrounding region, two sets of matrix equations from Equations (3) and (14), above, are rewritten:

$$\begin{bmatrix} A_{II} & A_{Ib} \\ A_{bI} & A_{bb} \end{bmatrix} \begin{Bmatrix} E_I \\ E_b \end{Bmatrix} = \begin{bmatrix} 0 & 0 \\ 0 & B_{bb} \end{bmatrix} \begin{Bmatrix} 0 \\ F_b \end{Bmatrix} \quad (17)$$

which is the FE system of equations and $$\begin{bmatrix} D_{bb} & 0 \\ D_{Ab} & 0 \end{bmatrix} \begin{Bmatrix} E_b \\ 0 \end{Bmatrix} = \begin{bmatrix} C_{bb} & C_{bA} \\ C_{Ab} & C_{AA} \end{bmatrix} \begin{Bmatrix} F_b \\ F_A \end{Bmatrix} + \begin{Bmatrix} Z_b \\ Z_A \end{Bmatrix} \quad (18)$$

which is the BE system of equations for their corresponding regions. Notationally, $E_I$ and $E_b$ are the electric field values at the interior and boundary nodes, respectively; $F_b$ is the flux (i.e., $F = \nabla E_z \cdot \hat{n}$) at the boundary and $F_A$ is the flux at the antenna array elements. $Z_b$ is a column vector whose entries are $Z_i = \langle fG_i \rangle$ for each boundary node with $Z_A$ being identical except that the Green's function is singular at the nonactive antenna array elements. Coefficients I, b, and A correspond to (1) nodes with the FE domain but not on its boundary, (2) nodes on the FE boundary, and (3) nodes representing the antenna array elements, respectively.

Derivation of the inverse scattering problem begins by differentiating both sets of equations with respect to the complex wavenumber squared, $k_j^2$, at node j. After the Newton-Raphson iterative process, the resultant vector, $\{k^2\}$, will comprise the image of the electrical property distribution. Differentiating Equations (17) and (18) with respect to $k_j^2$ within the target region produces:

$$\begin{bmatrix} \partial_j A_{II} & \partial_j A_{Ib} \\ \partial_j A_{bI} & \partial_j A_{bb} \end{bmatrix} \begin{Bmatrix} E_I \\ E_b \end{Bmatrix} + \begin{bmatrix} A_{II} & A_{Ib} \\ A_{bI} & A_{bb} \end{bmatrix} \begin{Bmatrix} \partial_j E_I \\ \partial_j E_b \end{Bmatrix} = \begin{bmatrix} 0 & 0 \\ 0 & B_{bb} \end{bmatrix} \begin{Bmatrix} 0 \\ \partial_j F_b \end{Bmatrix} \quad (19)$$

$$\begin{bmatrix} D_{bb} & 0 \\ D_{Ab} & 0 \end{bmatrix} \begin{Bmatrix} \partial_j E_b \\ 0 \end{Bmatrix} = \begin{bmatrix} C_{bb} & C_{bA} \\ C_{Ab} & C_{AA} \end{bmatrix} \begin{Bmatrix} \partial_j F_b \\ \partial_j F_A \end{Bmatrix} \quad (20)$$

where $\partial_j$ represents the partial derivative with respect to $k_j^2$ and $\partial_j B_{bb} = \partial_j D = \partial_j C = 0$ and $\partial_j Z_b = \partial_j Z_A = 0$ because these matrix contributions are not functions of $k_j^2$. Equation (20) is nearly identical to Equation (18), with the exception that the $\{E\}$ and $\{F\}$ terms have been replaced by $\{\partial_j E\}$ and $\{\partial_j F\}$, respectively, and the $\{Z_b Z_A\}^T$ term has been eliminated. Rearranging Equation (20) produces expressions for $\{\partial_j F_b\}$ and $\{\partial_j F_A\}$ solely in terms of the unknown $\{\partial_j E_b\}$:

$$\begin{Bmatrix} \partial_j F_b \\ \partial_j F_A \end{Bmatrix} = \begin{bmatrix} C_{bb} & C_{bA} \\ C_{Ab} & C_{AA} \end{bmatrix}^{-1} \begin{bmatrix} D_{bb} & 0 \\ D_{Ab} & 0 \end{bmatrix} \begin{Bmatrix} \partial_j E_b \\ 0 \end{Bmatrix} \quad (21)$$

Defining $[G] = [C]^{-1}[D]$, extracting just the expression for $\{\partial_j F_b\}$ and inserting it into Equation (19) yields (with some rearranging):

$$\begin{bmatrix} A_{II} & A_{Ib} \\ A_{bI} & A_{bb} - B_{bb} G_{bb} \end{bmatrix} \begin{Bmatrix} \partial_j E_I \\ \partial_j E_b \end{Bmatrix} = -\begin{bmatrix} \partial_j A_{II} & \partial_j A_{Ib} \\ \partial_j A_{bI} & \partial_j A_{bb} \end{bmatrix} \begin{Bmatrix} E_I \\ E_b \end{Bmatrix} \quad (22)$$

It should be noted that at each iteration of the procedure, the forward solution is produced utilizing the most current estimate of the $\{k^2\}$ distribution. Thus, in terms of Equation (22), the values of $\{E_I\}$ and $\{E_b\}$ are known. Additionally, the matrix on the left hand side of Equation (22) is identical to that used to compute the forward solution and typically is factored using an LU decomposition technique; whereas, the matrix on the right hand side of the equation is readily computed. Once $\{\partial_j E_b\}$ is determined, $\{\partial_j F_b\}$ and $\{\partial_j F_A\}$ can be assembled using Equation (21), and finally $\{\partial_j E_A\}$ is computed using the impedance condition relationship on the boundary of each antenna in the array, $E = -j\gamma \partial_n E$, with $\gamma$ being the effective impedance factor and $\partial_n$ being the partial derivative in the normal direction.

Similarly, the derivatives of the electric field values at the measurement sites with respect to $k_j^2$, $\{\partial_j E_x\}$, are computed by differentiating Equation (7) to yield:

$$\{\partial_j E_x\} = [D_{xb} D_{xA}] \begin{Bmatrix} \partial_j E_b \\ \partial_j E_A \end{Bmatrix} + [C_{xb} C_{xA}] \begin{Bmatrix} \partial_j F_b \\ \partial_j F_A \end{Bmatrix} \quad (23)$$

where $\partial_j E_x$ are the derivatives of the electric fields calculated at the set of measurement sites $x_1, x_2 \ldots x_m$ outside the target region. $D_{xb}$, $D_{xA}$, $C_{xb}$, and $C_{xA}$ are similar to their counterparts in Equation (18), except that the distance used in the Green's function argument extends from each measurement site to the boundary element integration path along either the imaging region boundary or the other nonactive antenna surfaces.

The electrical property distribution is updated at each iteration using the relationship:

$$\{k_{p+1}^2\} = \{k_p^2\} + \{\Delta k_p^2\} \quad (24)$$

with the electrical property update, $\{\Delta k_p^2\}$, computed at each iteration p from the regularized least squares minimization of the difference between computed and measured field quantities:

$$[J^T J + \lambda I]\{\Delta K_p^2\} = [J^T]\{E^C - E^M\} \quad (25)$$

where $E^C$ and $E^M$ represent the computed and measured field quantities, respectively; $\lambda$ is the regularization parameter; and J is the Jacobian matrix consisting of derivatives of the field distribution at each measurement site with respect to each property parameter variable to be determined. Specifically, the N columns of the Jacobian matrix are simply made up of the vector computed from Equation (23), $\{\partial_j E_x\}$, for j=1 to N, where N is the number of reconstructed parameters.

A method in accordance with the invention includes an improved regularization procedure. Generally, microwave imaging is an ill-posed problem. This means that in reconstructing an image, the procedure generally diverges to some meaningless solution unless some sort of regularization is applied. Regularization may come in different forms. A common technique is a Marquardt regularization, which can be described as follows.

A reconstruction algorithm typically includes three steps: (1) construct Jacobian matrix, (2) compute perturbation vector ($\Delta k^2$), and (3) update value of $k^2$ and recompute the electric fields.

Once the Jacobian matrix is formed, the following equation $$[J]\{\Delta k_p^2\} = \{E^m - E^c\} \quad (26)$$

is obtained, where [J] is the Jacobian matrix, $\{\Delta k_p^2\}$ is the perturbation vector at iteration p, and $\{E^m - E^c\}$ is the electric field difference vector between the measured and computed electric field values. To solve this, both sides of the equation are multiplied by $[J^T]$, the transpose of the Jacobian, to produce:

$$[J^T J]\{\Delta k_p^2\} = [J^T]\{E^m - E^c\} \quad (27)$$

where $[J^T J]$ is called the Hessian matrix. At this stage, the equation must be regularized so that it will converge. First, the system of equations is normalized. To do this, the diagonal matrix D is formed, which is simply the diagonal of $[J^T J]$ with zeros everywhere else. Then, $[J^T J]$ is pre- and post-multiplied by $[D^{1/2}] \cdot [D^{-1/2}]$ to get:

$$[[D^{1/2}][D^{-1/2}][J^T J][D^{-1/2}][D^{1/2}]]\{\Delta k_p^2\} = [J^T]\{E^m - E^c\} \quad (28)$$

The components of the matrix on the left are then re-grouped to form:

$$[[D^{-1/2}][J^T J][D^{-1/2}]]\{[D^{1/2}]\{\Delta k_p^2\}\} = [D^{-1/2}][J^T]\}E^m - E^c \quad (29)$$

In addition, a diagonal matrix, $[\lambda I]$, is added to $[[D^{-1/2}][J^T J][D^{-1/2}]]$ to produce:

$$[[D^{-1/2}][J^T J][D^{-1/2}] + [\lambda I]]\{[D^{1/2}]\{\Delta k_p^2\}\} = [D^{-1/2}][J^T J]\{E^m - E^c\} \quad (30)$$

$\lambda$ is chosen empirically and it is reduced at each iteration until the solution converges.

In this way, as A approaches zero, Equation (30) approaches Equation (29). The system of equations is then solved for $\{[D^{1/2}]\{\Delta k_p^2\}\}$ at each iteration, and then $\{\Delta k_p^2\}$ can be easily recovered through multiplication of $[D^{-1/2}]$. The updating of the $k^2$ values at each iteration is performed by the following equation:

$$\{k_{p+1}^2\} = \{k_p^2\} + \{\Delta k_p^2\} \quad (31)$$

where $\{k_p^2\}$ are the $k^2$ values at the current iteration and $\{k_{p+1}^2\}$ are the values at the next.

In addition to this technique, a spatial filtering technique is employed after each iteration. This tends to smooth out the final solution, but also has the beneficial effect of keeping the solution from diverging. It can be summarized as:

$$k_{smoothed}^2(A) = (1 - \Theta)k^2(A) + \frac{\Theta}{N} \sum_i^N k^2(A_i) \quad (32)$$

where $k^2(A)$ is the $k^2$ value at a coarse mesh node A before smoothing, and $k_{smoothed}^2(A)$ is its value afterwards. $A_i$ are the nodes attached to node A in the coarse finite element mesh (of which there are N), and $\Theta$ is a smoothing factor ranging from 0 to 1. This is applied for each value of $k^2$ in the coarse mesh. Since it is a linear procedure, it can be written in matrix form as:

$$[F_1]\{k_{smoothed}^2\}\{k^2\} \quad (33)$$

where the matrix, $F_1$ takes on the function of Equation (31), but in matrix form.

An improved reconstruction algorithm in accordance with the invention includes a novel approach that is a hybrid of the Marquardt technique and another technique, that is, a true Tikhonov regularization scheme. Two important points must be considered when the Tikhonov is used: (1) it works best when a good initial guess of the property distribution is given, and (2) the regularization parameter needs to be determined. It has been found that the Marquardt scheme with the spatial filtering technique provides an excellent (albeit very smoothed out) initial guess of the property distribution. Thus, the Marquardt scheme is used to provide an initial guess for the Tikhonov algorithm, which then recovers a more refined image of the electrical properties. Methods for choosing the regularization parameter are known in the art.

If a conventional Marquardt approach were to provide a true least squares solution, then taking those results and inputting them into the Tikhonov algorithm would achieve nothing. However, because so much smoothing is usually performed in this implementation, it is not a true least squares solution. Although the Marquardt and Tikhonov schemes are known, their combination is novel and provides significant enhancement.

The Tikhonov regularization technique is briefly described, as follows. It begins with the statement to be minimized:

$$\min|E^m-E^c|^2+\rho|k^2-k_o^2|^2 \quad (34)$$

The main difference between this and a conventional approach is the inclusion of the second term on the right, referred to as a penalty term. $\rho$ is called the regularization parameter, and $k_o^2$ is the initial guess of the electrical property distribution. In a standard derivation, a set of matrix equations that achieves this is:

$$[J^TJ+\lambda I]\{\Delta k_p^2\}=[J^T]\{E^m-E^c\}\rho\{k_p^2-k_o^2\} \quad (35)$$

where $k_p^2$ is the electrical property distribution at the current iteration. In very real terms, this is not that different from a conventional Marquardt approach, except for the addition of the second term on the right. The effect of this is to restrict the technique to solutions that are not too different from the original solution. The concept of "not too far" is defined by the size of $\rho$. If p is very large, the second term will dominate the process, and the final solution using the Tikhonov approach will essentially be the same as the original guess. If $\rho$ is too small, it is quite possible that the technique will diverge from a meaningful solution. However, with an optimal choice of $\rho$, it is possible to achieve significant image enhancement over prior techniques. The Tikhonov technique alone would not work as well as this hybrid approach since it would not be able to produce such a good initial guess, and it would be necessary to employ a much larger value of $\rho$ simply to keep the algorithm from diverging.

An electric field can be represented as a cosine wave:

$$E(t)=E_o \cos(\omega t+\phi) \quad (36)$$

where $\omega$ is the frequency in radians, t is time, $\phi$ is some arbitrary phase, and $E_o$ is an amplitude.

It can be re-written in complex form assuming a time-harmonic variation (removing the time dependence):

$$E_{complex}=E_R+jE_I \quad (37)$$

where j is $\sqrt{-1}$ and $E_R$ and $E_I$ are its real and imaginary components. It is often convenient to express them in their log-magnitude and phase form:

$$E_{mag}=\log[(E_R^2+E_I^2)^{1/2}]$$

$$E_{phase}=a\tan(E_I/E_R) \quad (38)$$

To express the $E_{mag}$ portion in terms of decibels, simply multiply $E_{mag}$ by 20. In general, in a method and a system in accordance with the invention, one period of the cosine wave, E(t), is sampled, converted to its complex form, and then converted to its log-magnitude and phase form for phase unwrapping.

In the microwave imaging of high contrast objects (high compared to the saline or water background), even at relatively low frequencies, the phase changes detected at a single receiver by the data acquisition system can exceed $\pi$ radians. In fact, as the operating frequency is increased to improve the image quality, the measured phase change will be even greater for a given target. This poses problems when the measured field data is expressed in its complex number form because information about multiple phase wrappings in the measured data is lost, potentially introducing ambiguity into the solution. In these cases, it may be difficult to determine whether the recovery of an inadequate microwave image is truly due to non-uniqueness related to non-radiating sources orto loss of information from phase wrapping. A method and a system in accordance with the invention implement a version of a Newton-Raphson based reconstruction algorithm that utilizes the phases and the logarithm of the magnitudes of the measured and computed electric field values at each iteration, respectively. It implements simple strategies for these unwrapping tasks that are conveniently incorporated into the forward scattering model and the geometry of the illumination region.

Unwrapping of scattered computed 2D forward data typically includes: calculating electric field values at a plurality of computation points between the antennae; choosing a reference computation point close to the active transmitting antenna; and comparing phase values at the computation point and a neighboring computation point to determine an unwrapped phase value at the neighboring computation point. In the currently preferred method, a reference computation point is chosen at about 2.7 mm distance from the active transmitting antenna. The next calculation in sequence is performed at a neighboring computation point located at a distance of about $\lambda_{water}/10$, that is, the signal wavelength in water divided by 10. The value $\lambda_{water}$ may be calculated as follows:

$\lambda_{air}$=speed of light/frequency of light;

$\lambda_{water}=\lambda_{air} \times 1/[(\epsilon_r)^{1/2}]$

At high frequencies, the physical receive-antenna separation is electrically large enough to render unwrapping the measured phase data with respect to adjacent receiver data impossible. However, by collecting the data over a broad frequency range, the data are easily unwrapped at the lowest frequency, and the data for each transmit/receive antenna pair for successively higher frequencies can be easily unwrapped by comparison with its corresponding data from the previous, lower frequency. The ability of a system in accordance with the invention to acquire new measurement data over a broad frequency range is essential to the ability to unwrap the phases.

Unwrapping the electric field values in a preferred method includes, therefore, unwrapping scattered field data. A first phase value is determined at 300 MHz. A second, wrapped face value is then measured at the receiving antenna at 350 MHz. The second, wrapped phase value is compared with the first, unwrapped phase value to obtain a second, unwrapped phase value at 350 MHz. Subsequent measurements are conducted at a 50 MHz increment above the previous frequency, and the procedure is repeated until the highest frequency of 3 GHz is achieved.

In performing the image reconstructions, a method in accordance with the invention compares the scattered field data with the scattered computed 2D forward data at each iteration in their log-magnitude and phase form. This is in contrast to earlier methods, in which calibrated field data was compared with computed 2D forward data at each iteration in their real and imaginary form. The following terminology is useful for understanding the distinctions just explained between the prior art and a method in accordance with the present invention.

"Calibration data" means measured electric field data at each vertical position and operating frequency for all possible transmit and receive antenna pairs when the illumination chamber is filled with the liquid homogeneous medium and some phantom target with known size and electrical properties.

"Measured data" are the measured electric field data at each vertical position and operating frequency for all possible transmit and receive antenna pairs when an inhomogeneous target is pendant in the illumination region.

"Scattered field data" are the measured data with the calibration data subtracted from them (in terms of magnitude and phase form, and not in real and imaginary form).

"Computed 2D forward calibration data" are the electric field values computed using a 2D numerical model with the measurement sides corresponding exactly to those in the actual illumination region, and with the electrical properties of the modeled illumination region having exactly the same values as those of the corresponding illumination region when the calibration data was acquired.

"Calibrated data" means the scattered field data added to the computed 2D forward calibration data (in terms of magnitude and phase, and not in real and imaginary form).

"Computed 2D forward data" are the electric field values computed using a 2D numerical model; the measurement sites correspond exactly to those in the actual illumination region, and electrical properties of the modeled illumination region reflect the property distribution at a given iteration within the image reconstruction process.

"Scattered computed 2D forward data" are the computed 2D forward data with the computed 2D forward calibration data subtracted from them (in terms of magnitude and phase, and not in real and imaginary form).

"Wrapped phase data" generally refer to either scattered field data or scattered computed 2D forward data. There are many cases when the presence of high contrast objects may cause the phases of the interrogating electric fields to exceed the bounds of $-\pi$ to $+\pi$. In a conventional scheme, the phases are automatically restricted to these bounds by addition or subtraction of the appropriate multiples of $2\pi$. These phase values are considered to be wrapped.

"Unwrapped phase data" means either scattered field data or scattered computed 2D forward data. There are many cases when the presence of high contrast objects may cause the phases of the interrogating electric fields to exceed the bounds of $-\pi$ to $+\pi$. Unwrapped phase data may exceed these values, but can only be deduced with the knowledge of phases at the same location for frequencies stepped up to the phases of the current operating frequency in small increments, or with knowledge of the unwrapped phase values in a very near physical proximity. This can only be represented in the magnitude/phase format, and not in the real and imaginary format.

Thus, all of the calibration is performed while data are in their log-magnitude and phase form. They are typically converted back to the complex form for use in the reconstruction algorithms described above.

There has been described a method and apparatus for microwave imaging of inhomogeneous targets, in particular, of biological tissue. It should be understood that the particular embodiments shown in the drawings and described within this specification are for purposes of example and should not be construed to limit the invention which will be described in the claims below. Further, it is evident that those skilled in the art may now make numerous uses and modifications of the specific embodiment described, without departing from the inventive concepts. It is also evident that the steps recited may in some instances be performed in a different order; or equivalent structures and processes may be substituted for the various structures and processes described. Consequently, the invention is to be construed as embracing each and every novel feature and novel combination of features present in and/or possessed by the electronic devices, structures, computational methods of processing data, and mathematical models described.

What is claimed is:

1. In a method of determining electrical properties of an inhomogeneous target, including steps of measuring electric field values external to said target using an antenna array, in which an active transmitting antenna transmits a microwave signal, and an active receiving antenna receives said microwave signal, and steps of using said measured electric field values with a mathematical model to compute an electric property distribution in said target, the improvement to compensate for the effect of a nonactive antenna of the array on said measured electric field values comprising steps of:

presenting a matched termination to a nonactive antenna of an antenna array; and modeling said nonactive antenna as an electromagnetic sink in a numerical model.

2. A method as in claim 1, characterized in that said step of presenting a matched termination to said nonactive antenna comprises attaching said nonactive antenna via a coaxial connection to a coaxial matched load.

3. A method as in claim 1, characterized in that said step of presenting a matched termination to said nonactive antenna comprises attaching said nonactive antenna via a coaxial connection to a matched switch.

4. A method as in claim 1, characterized in that said step of presenting a matched termination to said nonactive antenna comprises attaching said nonactive antenna via a coaxial connection to a well-matched amplifier.

5. A method as in claim 1, further characterized by steps of:

computing an electric field value at said nonactive antenna.

6. In a method as in claim 1, a further improvement characterized in that said modeling said nonactive antenna as an electromagnetic sink comprises:

modeling said nonactive antenna as a finite diameter circle having a circular boundary; and imposing a radiation type boundary condition on said boundary.

7. In a method as in claim 6, a further improvement characterized in that said modeling includes empirically determining an effective radius and an effective impedance of said nonactive antenna.

8. In a method as in claim 7, a further improvement characterized in that said empirically determining said effective radius and said effective impedance comprises measuring electric field values at a plurality of frequencies in a range of from 300 MHz to 3 GHz.

9. In a method as in claim 8, a further improvement characterized in that said empirically determining said effective radius and said effective impedance comprises measuring an electric field value when said nonactive antenna is present and when said nonactive antenna is not present.

10. In a method of determining electrical properties of an inhomogeneous target, including steps of measuring electric field values external to a boundary that defines said target using an antenna array having a plurality of antennae, in which an active transmitting antenna transmits a microwave signal, and an active receiving antenna receives said microwave signal, and steps of using said measured electric field values with a mathematical model to compute an electrical property distribution in said target, the improvement comprising:

steps of reconstructing the electrical property distribution by directly utilizing log-magnitude and phase forms of field data selected from the group consisting of scattered field data, calibrated data, computed 2D forward data, and scattered computed 2D forward data.

11. In a method as in claim 10, a further improvement characterized in that said reconstructing comprises unwrapping phase values of field data selected from the group consisting of scattered field data, calibrated data, computed 2D forward data, and scattered computed 2D forward data.

12. In a method as in claim 11, a further improvement characterized in that said unwrapping phase values of field data selected from the group consisting of scattered computed 2D forward data and computed 2D forward data comprises:
    calculating electric field values at a plurality of computation points between said antennae;
    choosing a reference computation point close to said active transmitting antenna; and
    comparing phase values at said computation point and a neighboring computation point to determine an unwrapped phase value at said neighboring computation point.

13. In a method as in claim 11, a further improvement characterized in that said unwrapping phase values of field data selected from the group consisting of scattered field data and calibrated data comprises:
    determining a first, unwrapped phase value at said active receiving antenna at a first, low frequency;
    measuring a second, wrapped phase value at said receiving antenna at a second, high frequency; and
    then comparing said second, wrapped phase valuewith said first, unwrapped phase value to determine a second, unwrapped phase value.

14. A method as in claim 13, further characterized in that said first low-frequency has a low value in a range of from 300 MHz to 3 GHz, and said second high frequency has a high value that is about 50 MHz higher than said low value.

15. In a method of determining electrical properties of an inhomogeneous target, including steps of measuring electric field values external to said target using an antenna array, and steps of using said measured electric field values with a mathematical model to compute an electrical property distribution in a coarse mesh discretization of a target region, the improvement comprising:
    performing a first reconstruction, thereby determining a perimeter of said target; and
    calculating a new fine mesh and a new coarse mesh of the target region, said new meshes conforming to said perimeter.

16. In a method as in claim 15, a further improvement characterized in that said target is surrounded by a homogeneous medium, and said perimeter corresponds to an interface between said target and said homogeneous medium.

17. In a method as in claim 15, a further improvement characterized in that said homogeneous medium is a saline bath.

18. In a method as in claim 15, a further improvement characterized in that said target comprises biological tissue.

19. In a method as in claim 18, a further improvement characterized in that said target is a human female breast.

20. In a method of determining electrical properties of an inhomogeneous target, including steps of measuring electric field values external to said target using an antenna array, and steps of using said measured electric field values with a mathematical model to compute an electrical property distribution in a coarse mesh discretization of a target region, the improvement comprising:
    using a Marquardt regularization scheme combined with a Tikhonov regularization scheme.

21. A method as in claim 20, characterized in that said Marquardt scheme, in conjunction with a spatial filtering technique, provides an initial reconstruction of said electrical property distribution, and said Tikhonov scheme thereafter computes a refined reconstruction of said electrical property distribution.

22. In a system for determining electrical properties of an inhomogeneous target, comprising an illumination chamber containing a homogeneous medium having substantially homogeneous electrical properties and in which said inhomogeneous target may be disposed, and an antenna array having a plurality of antennae disposed within said homogeneous medium for transmitting and alternately receiving microwave energy, the improvement characterized in that:
    said antenna array comprises a plurality of inverted monopole antennae.

23. In a system as in claim 22, a further improvement characterized in that said system operates over a frequency band in a range of from 300 MHz to 3 GHz.

24. In a system as in claim 22, a further improvement characterized in that said homogeneous region comprises a saline solution.

25. In a system as in claim 22, a further improvement characterized in that said homogeneous region comprises water.

26. In a system as in claim 22, a further improvement characterized in that said antenna array includes a nonactive antenna and said system comprises a microwave switching network for presenting said nonactive antenna with a matched termination.

27. A system as in claim 26, further characterized in that said system comprises a matched switch and a coaxial connection, said coaxial connection disposed between said nonactive antenna and said matched switch.

28. A system as in claim 26, further characterized in that said system comprises a single pole-double throw (SPDT) switch, a well-matched amplifier, and a coaxial connection, said coaxial connection disposed between said nonactive antenna and said single pole-double throw (SPDT) switch, said single pole-double throw (SPDT) switch being connected to said well-matched amplifier.

29. In a system as in claim 22, a further improvement characterized by an A/D board capable of simultaneously sampling signals received by a plurality of said antennae.

30. In a system as in claim 22, a further improvement characterized in that said antenna array is movable to multiple vertical positions.

31. In a system as in claim 22, a further improvement characterized in that said system comprises an electronically controllable linear translation stage for moving said antenna array.

32. In a system as in claim 22, a further improvement characterized in that said antenna array is mounted to a solid array plate.

33. In a system as in claim 22, a further improvement characterized in that said system comprises protective bellows for protecting electrical wires connected to said antennae.

34. In a system as in claim 22, a further improvement characterized in that said system comprises a rigid sheet disposed above said homogeneous medium and having a hole for accommodating said inhomogeneous target.

35. In a system for determining electrical properties of an inhomogeneous target, comprising an illumination chamber containing a homogeneous medium having substantially homogeneous electrical properties and in which said inhomogeneous target may be disposed, and an antenna array having a plurality of antennae disposed within said homogeneous medium, the improvement characterized by:

a microwave switching network for presenting a nonactive antenna with a matched termination.

* * * * *

UNITED STATES PATENT AND TRADEMARK OFFICE
CERTIFICATE OF CORRECTION

PATENT NO. : 6,448,788 B1
DATED : September 10, 2002
INVENTOR(S) : Paul M. Meaney, Keith D. Paulsen and Margaret W. Fanning It is certified that error appears in the above-identified patent and that said Letters Patent is hereby corrected as shown below:

Column 1,
Line 49, "properties $\in_r$" should read -- properties $\varepsilon_r$ --; and
Line 56, "$\in_r$ and $\sigma$ (i.e., $k^2=\omega\mu\in_r\in_o +j\omega\mu\sigma$, where $\in_o$" should read
-- $\varepsilon_r$ and $\sigma$ (i.e., $k^2=\omega\mu\varepsilon_r\varepsilon_o +j\omega\mu\sigma$, where $\varepsilon_o$ --; and
Line 57, "$\in_r$" should read -- $\varepsilon_r$ --.

Column 2,
Line 19, "$[A]\{\bar{E}\}=\{\bar{b}\}.$" should read -- $[A]\{\bar{E}\}=\{\bar{b}\}.$ --.

Column 3,
Lines 52 and 54, "$\in_r$" should read -- $\varepsilon_r$ --; and
Line 56, "$\in_r$, of 1.0, and the dielectric constant, $\in_r$" should read
-- $\varepsilon_r$, of 1.0, and the dielectric constant, $\varepsilon_r$ --.

Column 8,
Line 45, "targevsaline" should read -- target/saline --.

Column 10,
Line 36, "$\in_r$" should read -- $\varepsilon_r$ --; and
Line 52, "transmit receive" should read -- transmit/receive --.

Column 11,
Line 11, "$\omega^2\mu\in$)" should read -- $\omega^2\mu\varepsilon$) -- ; and
Line 12, "f=$\delta(x_s,y_s)$" should read -- f = A$\delta(x_s,y_s)$ --; and
Line 23, "$\oint$ represents its enclosing surface" should read
-- $\oint$ represents the line integral around its enclosing surface--; and Line 26, "$E_z$ is the basis-function expanded in" should read
-- $E_z$ is the basis-function expanded electric field in --; and Lines 30-31, "$\begin{bmatrix} A_{II} & A_{Ib} \\ A_{bI} & A_{bb} \end{bmatrix}\begin{Bmatrix} E_I \\ E_b \end{Bmatrix} = \begin{bmatrix} 00 & \\ 0B_{bb} & \end{bmatrix}\begin{Bmatrix} 0 \\ F_b \end{Bmatrix}$" should read -- $\begin{bmatrix} A_{II} & A_{Ib} \\ A_{bI} & A_{bb} \end{bmatrix}\begin{Bmatrix} E_I \\ E_b \end{Bmatrix} = \begin{bmatrix} 0 & 0 \\ 0 & B_{bb} \end{bmatrix}\begin{Bmatrix} 0 \\ F_b \end{Bmatrix}$ --; and

UNITED STATES PATENT AND TRADEMARK OFFICE
CERTIFICATE OF CORRECTION

PATENT NO. : 6,448,788 B1
DATED : September 10, 2002
INVENTOR(S) : Paul M. Meaney, Keith D. Paulsen and Margaret W. Fanning It is certified that error appears in the above-identified patent and that said Letters Patent is hereby corrected as shown below:

Column 11, (cont'd),
Line 40, "$A_{1I}A_{1b}$" should read -- $A_{II}$, $A_{Ib}$ --; and
Line 44, "(i.e., $A_{1I}$)" should read -- (i.e., $A_{II}$) --; and
Line 45, "(i.e $A_{Ib},A_{bI}$)" should read -- (i.e. $A_{Ib}$, $A_{bI}$) --.

Column 12,
Lines 6-7, "$d_{ij}=\alpha_i+\circ \int \nabla G_i \cdot \hat{n} \phi_j ds$" should read -- $d_{ij} = \alpha_i + \oint \nabla G_i \cdot \hat{n} \phi_j ds$ --; and Lines 30, "Dxb, Cxband $Z_x$" should read -- $D_{xb}$, $C_{xb}$ and $Z_x$ --.

Column 13,
Line 43, "where and $\partial_n G_i = \partial_R G_i(\hat{R}_i \cdot \hat{n}))$" should read -- where $\partial_n G_i = \partial_R G_i(\hat{R}_i \cdot \hat{n})$ --.

Column 14,
Line 56, "$G_{bb} = Cl_{bb}D_{bb}+Cl_{bA}D_{Ab}$ and $Cl = C^{-b}$" should read
-- $G_{bb} = Cl_{bb}D_{bb}+Cl_{bA}D_{Ab}$ and $Cl = C^{-1}$ --

Column 16,
Line 44, "the $\{Z_b Z_A\}^T$ term" should read -- the $\{Z_b\ Z_A\}^T$ term --.

Column 17,
Lines 12-13, "$[\partial_j E_x] = [D_{xb} D_{xA}]\begin{Bmatrix}\partial_j E_b \\ \partial_j E_A\end{Bmatrix} + [C_{xb} C_{xA}]\begin{Bmatrix}\partial_j F_b \\ \partial_j F_A\end{Bmatrix}$"

should read -- $[\partial_j E_x] = [D_{xb}\ \ D_{xA}]\begin{Bmatrix}\partial_j E_b \\ \partial_j E_A\end{Bmatrix} + [C_{xb}\ \ C_{xA}]\begin{Bmatrix}\partial_j F_b \\ \partial_j F_A\end{Bmatrix}$ --

Line 26, "$\{k_p+{}_i^2\}$" should read -- $\{k_{p+1}^2\}$ --;
Line 32, "$\{\Delta K_p^{\ 2}\}$" should read -- $\{\Delta k_p^2\}$ --; and
Line 41, "$\{\partial_j E_x\}$," should read -- $\{\partial_j E_x\}$, --.

Column 18,
Line 12, "$[D^{-1/2}{}_l][J^T]]E^m-E^c$" should read -- $[D^{-1/2}][J^T]\{E^m-E^c\}$ --; and
Lines 19-20,
"until the solution converges.
    In this way, as A approaches zero, Equation (30)" should read
-- until the solution converges. In this way, as λ approaches zero, Equation (30) --; and
Line 47, "$[F_1]\{k^2_{smoothed}\}\ \{k^2\}$" should read -- $[F_1]\{k^2_{smoothed}\} = \{k^2\}$ --; and
Line 49, "Equation (31)" should read -- Equation (32) --.

UNITED STATES PATENT AND TRADEMARK OFFICE
CERTIFICATE OF CORRECTION

PATENT NO. : 6,448,788 B1
DATED : September 10, 2002
INVENTOR(S) : Paul M. Meaney, Keith D. Paulsen and Margaret W. Fanning It is certified that error appears in the above-identified patent and that said Letters Patent is hereby corrected as shown below:

Column 19,
Line 27, "If p is very large" should read -- If $\rho$ is very large --; and
Line 49, "$E_1$" should read -- $E_I$ --; and
Line 54, "$E_{phase}=_a \tan (E_I/E_R)$" should read -- $E_{phase} = \text{atan} (E_I/E_R)$ --.

Column 20,
Line 8, "orto" should read -- or to --; and
Line 33, "$\in_r$" should read -- $\varepsilon_r$ --.

Column 21,
Line 14, "sides" should read -- sites --.

Column 23,
Line 33, "valuewith" should read -- value with --.

Signed and Sealed this

Twelfth Day of April, 2005

JON W. DUDAS
*Director of the United States Patent and Trademark Office*